US010925643B2

(12) United States Patent
Melsheimer

(10) Patent No.: US 10,925,643 B2
(45) Date of Patent: Feb. 23, 2021

(54) INTRODUCER FOR UTERINE TAMPONADE ASSEMBLY AND METHODS OF USING THE SAME

(71) Applicant: COOK MEDICAL TECHNOLOGIES LLC, Bloomington, IN (US)

(72) Inventor: Jeffry S. Melsheimer, Springville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 238 days.

(21) Appl. No.: 16/003,323

(22) Filed: Jun. 8, 2018

(65) Prior Publication Data
US 2018/0360494 A1    Dec. 20, 2018

Related U.S. Application Data

(60) Provisional application No. 62/521,773, filed on Jun. 19, 2017.

(51) Int. Cl.
*A61M 25/01* (2006.01)
*A61B 17/42* (2006.01)
(Continued)

(52) U.S. Cl.
CPC .......... *A61B 17/42* (2013.01); *A61B 17/1204* (2013.01); *A61B 17/12099* (2013.01);
(Continued)

(58) Field of Classification Search
CPC .. A61M 2025/091; A61M 2025/09101; A61M 39/10; A61M 2025/09066;
(Continued)

(56) References Cited

U.S. PATENT DOCUMENTS 837,085 A    11/1906   Loar
3,822,702 A   7/1974   Bolduc
(Continued)

FOREIGN PATENT DOCUMENTS

DE      4225520 A1    2/1994
JP    2014100303 A *  6/2014
WO   WO-0057943 A9 *  7/2002  ............ A61M 25/09

OTHER PUBLICATIONS

Search Report and the Written Opinion for PCT/US2019/051100, dated Feb. 11, 2020, 18 pages.
(Continued)

*Primary Examiner* — Nathan R Price
*Assistant Examiner* — Anna E Goldberg-Richmeier
(74) *Attorney, Agent, or Firm* — Brinks Gilson & Lione

(57) ABSTRACT

A device for use with a uterine tamponade balloon catheter apparatus, such as the Bakri postpartum hemorrhage balloon, is disclosed. The device comprises a stylet comprising a hub at its proximal end. The device is configured to be removably coupled to the tamponade balloon catheter apparatus to aid in the insertion and positioning of the tamponade balloon catheter within the uterine cavity, allowing the balloon to function as intended for the control and management of postpartum hemorrhage and uterine bleeding. Methods of use of the device are also disclosed.

18 Claims, 4 Drawing Sheets

(51) Int. Cl.
  *A61B 17/12* (2006.01)
  *A61M 25/00* (2006.01)
  *A61B 17/34* (2006.01)
  *A61M 25/10* (2013.01)
  *A61B 17/00* (2006.01)

(52) U.S. Cl.
  CPC .... *A61B 17/12136* (2013.01); *A61B 17/3415* (2013.01); *A61M 25/0097* (2013.01); *A61M 25/0102* (2013.01); *A61B 2017/00278* (2013.01); *A61B 2017/12004* (2013.01); *A61B 2017/1205* (2013.01); *A61B 2017/345* (2013.01); *A61B 2017/4216* (2013.01); *A61M 2025/1061* (2013.01); *A61M 2025/1093* (2013.01); *A61M 2210/1433* (2013.01)

(58) Field of Classification Search
  CPC ...... A61M 25/0102; A61M 2025/1065; A61M 25/007; A61B 2217/005; A61B 17/42
  See application file for complete search history.

(56) References Cited

U.S. PATENT DOCUMENTS

| | | | |
|---|---|---|---|
| 4,207,891 A | 6/1980 | Bolduc | |
| 4,601,698 A | 7/1986 | Moulding | |
| D286,677 S | 11/1986 | Osborne | |
| 4,753,640 A | 6/1988 | Nichols et al. | |
| 4,964,854 A | 10/1990 | Luther | |
| 5,295,968 A | 3/1994 | Martel et al. | |
| 5,569,222 A * | 10/1996 | Haselhorst | A61M 39/12 |
| | | | 604/533 |
| 6,245,029 B1 | 6/2001 | Fujita et al. | |
| 6,395,012 B1 | 5/2002 | Yoon et al. | |
| D476,418 S | 6/2003 | Sprieck | |
| 6,740,095 B2 | 5/2004 | Watson | |
| 6,813,520 B2 | 11/2004 | Truckai | |
| D565,192 S | 3/2008 | Tajima | |
| D585,547 S | 1/2009 | Basleri | |
| D630,733 S | 1/2011 | Ahlgren | |
| D640,785 S | 6/2011 | Lee | |
| D663,832 S | 7/2012 | Essinger | |
| 8,282,612 B1 | 10/2012 | Miller | |
| 8,287,496 B2 * | 10/2012 | Racz | A61M 25/0606 |
| | | | 604/164.01 |
| D692,134 S | 10/2013 | Lee-Sepsick | |
| D699,341 S | 2/2014 | Clark | |
| 8,770,200 B2 | 7/2014 | Ahluwalia | |
| D713,957 S | 9/2014 | Woehr | |
| 9,028,401 B1 | 5/2015 | Bacich et al. | |
| 9,067,013 B2 | 6/2015 | Wright et al. | |
| D747,802 S | 1/2016 | Freigang | |
| D748,777 S | 2/2016 | Uenishi | |
| D751,704 S | 3/2016 | Corydon | |
| 9,364,638 B2 | 6/2016 | Duncan | |
| D772,411 S | 11/2016 | Heath | |
| D798,446 S | 9/2017 | Nino | |
| D816,217 S | 4/2018 | Naughton | |
| D846,116 S | 4/2019 | Naughton | |
| D854,148 S | 7/2019 | Prinz | |
| D859,651 S | 9/2019 | Harding | |
| 2004/0030352 A1 | 2/2004 | McGloughlin et al. | |
| 2005/0143689 A1 | 6/2005 | Ramsey, III | |
| 2005/0256532 A1 | 11/2005 | Nayak | |
| 2006/0015075 A1 | 1/2006 | Blanco | |
| 2006/0173486 A1 | 8/2006 | Burke et al. | |
| 2009/0157007 A1 | 6/2009 | McKinnon | |
| 2011/0060317 A1 | 3/2011 | Frojd | |
| 2011/0220120 A1 | 9/2011 | Frigstad et al. | |
| 2011/0259344 A1 | 10/2011 | Ahluwalia | |
| 2013/0204208 A1 | 8/2013 | Olson et al. | |
| 2014/0094773 A1 | 4/2014 | Lampropoulos et al. | |
| 2014/0158138 A1 | 6/2014 | Ziv et al. | |
| 2015/0051634 A1 | 2/2015 | Kravik et al. | |
| 2015/0202411 A1 * | 7/2015 | Duncan | A61M 25/04 |
| | | | 604/544 |
| 2015/0342641 A1 | 12/2015 | Belfort et al. | |
| 2016/0045719 A1 | 2/2016 | Ha et al. | |
| 2016/0100861 A1 | 4/2016 | Parys et al. | |
| 2016/0106466 A1 | 4/2016 | Gruber et al. | |
| 2016/0166282 A1 | 6/2016 | Juravic et al. | |
| 2016/0256301 A1 * | 9/2016 | Roeder | A61F 2/966 |
| 2017/0312432 A1 | 11/2017 | Huang | |
| 2018/0360494 A1 | 12/2018 | Melsheimer | |
| 2019/0059947 A1 | 2/2019 | Bunch et al. | |
| 2019/0110797 A1 | 4/2019 | Melsheimer | |

OTHER PUBLICATIONS

Partial International Search Report for corresponding PCT/US2018/036865, dated Aug. 31, 2018, 10 pages.
International Search Report and Written Opinion for corresponding PCT/US2018/036865, dated Oct. 23, 2018, 18 pages.
International Preliminary Report on Patentability and Written Opinion for PCT/US2018/036865, dated Dec. 24, 2019, 8 pages.
Invitation to Pay Additional Fees and Communication Relating to the Results of the Partial International Search for PCT/US2019/051100, dated Dec. 16, 2019, 11 pages.
Examination Report for Australian Application No. 2018288595, dated Apr. 20, 2020, 5 pages.
U.S. Appl. No. 16/046,327, filed Jul. 26, 2018.
U.S. Appl. No. 16/123,433, filed Sep. 6, 2018.
U.S. Appl. No. 16/570,034, filed Sep. 13, 2019.
Design U.S. Appl. No. 29/664,085, filed Sep. 21, 2018.

* cited by examiner

INTRODUCER FOR UTERINE TAMPONADE ASSEMBLY AND METHODS OF USING THE SAME

RELATED APPLICATIONS

This application claims the benefit of the filing date under 35 U.S.C. § 119(e) of Provisional U.S. Patent Application Ser. No. 62/521,773, filed Jun. 19, 2017, which is hereby incorporated by reference.

TECHNICAL FIELD

The present invention relates generally to apparatus and methods for controlling uterine bleeding, and more specifically, to an accessory device for use with a uterine tamponade assembly that facilitates proper insertion and positioning of the tamponade assembly within the uterus.

Uterine bleeding is a clinical condition attributable to a variety of causes, including postpartum hemorrhages (PPH) following vaginal and/or cesarean childbirth. Postpartum hemorrhage or excessive blood loss after childbirth is commonly caused by uterine atony whereby the uterus fails to contract normally after the delivery of a baby, leading to continuous bleeding. If left untreated, PPH may cause serious complications or even death.

There are a variety of techniques used for treating and managing PPH, including the administration of muscle contracting drugs or agents alone or in combination with other mechanical or surgical techniques. One such technique includes inserting a tamponade apparatus such as a balloon tamponade catheter into the uterus, wherein the balloon is inflated to a sufficient pressure and volume until it conforms generally to the contour of the uterine cavity. The application of pressure to the cervical canal and the interior uterine wall provides a tamponade effect until bleeding is controlled or stopped. One example of a uterine tamponade balloon catheter is the Bakri balloon, Cook Medical, Bloomington, Ind. The effectiveness of the Bakri balloon may be partially attributable to efficient and proper insertion, placement and inflation, as well as maintaining the balloon in a proper position within the uterine cavity.

In most cases, when use of a balloon tamponade catheter is required, the physician may insert the balloon portion of the catheter into the uterus, making certain that the entire balloon is inserted past the cervical canal and internal ostium. Insertion may be accomplished trans-vaginally following vaginal delivery or trans-abdominally following a cesarean delivery. It is therefore desirable to provide an accessory device, such as an introducer, that can remain in place during use and also serve as a positioner to maintain the proper positioning of the balloon tamponade catheter, which can be used to efficiently and effectively to accurately insert and position the balloon tamponade catheter within a patient's uterus. Accordingly, the disclosed introducer device can be used with various known uterine tamponade assemblies, such as the Bakri balloon. The disclosed introducer device may be utilized to rapidly introduce the tamponade assembly into the uterus and remain in place during use of the tamponade assembly, allowing the balloon to function as intended for the control and management of PPH and uterine bleeding. Advantageously, the disclosed introducer device is designed and configured to be used with a tamponade balloon assembly, while providing a desired combination of attributes and characteristics for its intended use, including, but not limited to, flexibility, torsion and malleability to navigate a patient's anatomy without causing trauma, while also having sufficient pushability and column strength to aid in insertion of the tamponade assembly and allowing adequate drainage if left in place during use of the tamponade balloon assembly.

SUMMARY

In one example, the present disclosure describes a catheter assembly comprising a positioning device comprising a stylet having a proximal end and a distal end and a hub at the proximal end of the stylet. The assembly further comprises a tamponade balloon catheter comprising a catheter comprising a proximal end and a distal end and at least one lumen extending there between and an expandable tamponade device at the distal end of the catheter wherein the stylet is configured to extend longitudinally within at least a portion of the length of the at least one catheter lumen.

The present disclosure further describes a positioning device comprising a stylet comprising a longitudinal body having a proximal end and a distal end and a hub at the proximal end of the stylet. The hub comprises a proximal end, a distal end and a sidewall extending there between defining a hub lumen, wherein the sidewall of the hub comprises at least one opening formed therein.

DETAILED DESCRIPTION

Throughout this specification, the terms proximal and proximally are used to refer to a position or direction away from, or even external to a patient's body and the terms distal and distally are used to refer to a position or direction towards the patient and/or to be inserted into a patient's body orifice or cavity. The embodiments described below are primarily in connection with an introducer device for use with, or as an accessory to, a tamponade assembly such as a tamponade balloon catheter for treating postpartum hemorrhage, and for introducing and positioning the tamponade balloon catheter in a desired position within the uterus. However, the described introducer device may also be used in connection with a range of medical instruments which are inserted into various body cavities to effectively and efficiently introduce and position such instruments depending on the technique or procedure being performed as will be appreciated by those of skill in the art.

Figure 1:
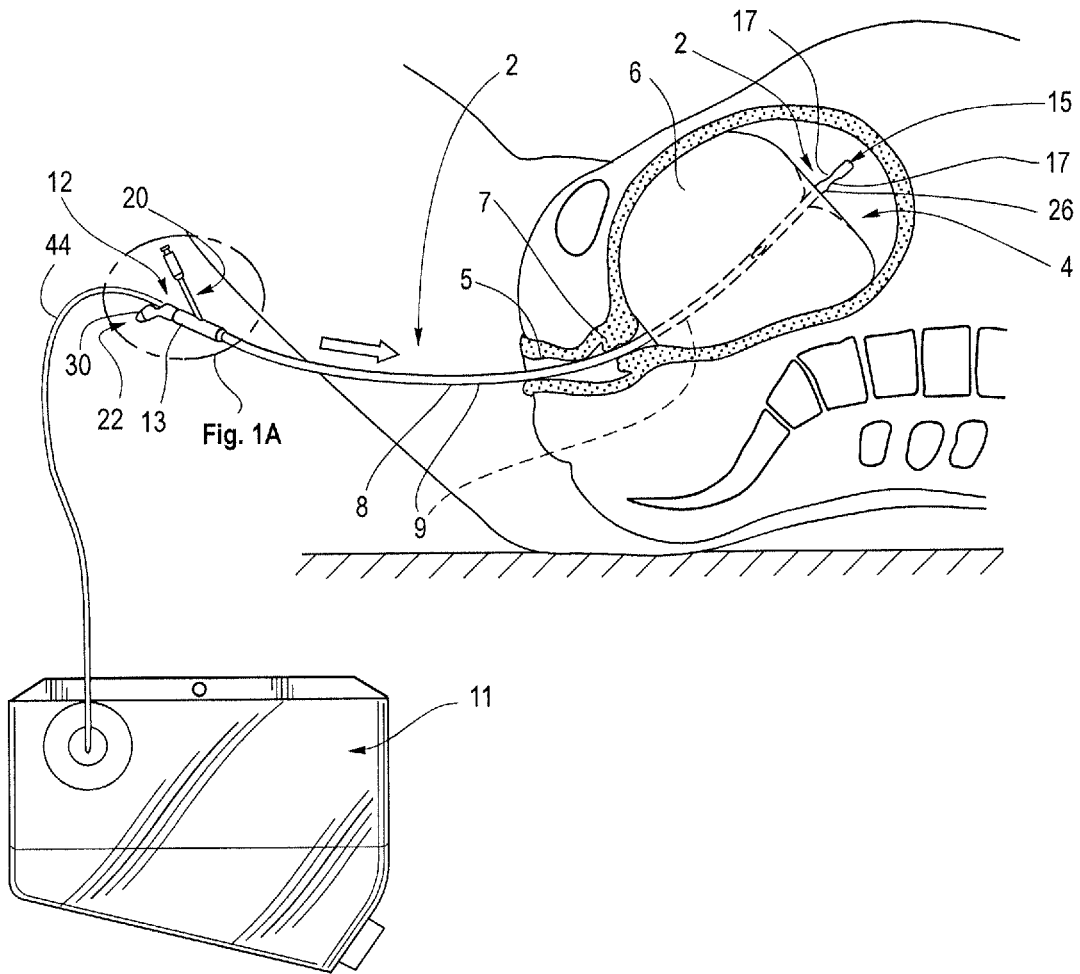
FIG. 1 is a side view of a patient's anatomy showing trans-vaginal insertion and inflation of a tamponade balloon catheter with an example of an introducer device coupled to the tamponade balloon catheter assembly in use to treat hemorrhage.
Figure 1A:
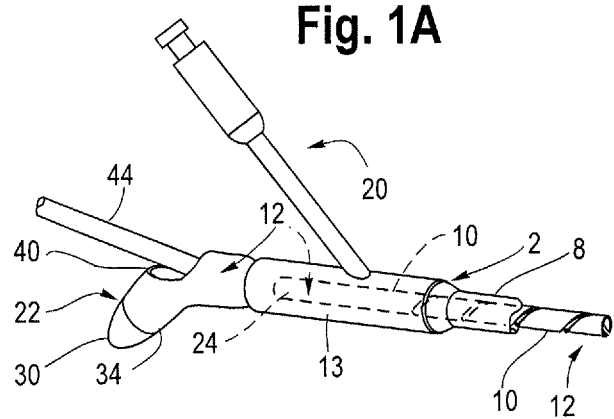
FIG. 1A is an enlargement of a portion of FIG. 1 illustrating a hub of an introducer device coupled to the proximal end of a tamponade balloon catheter assembly and a drainage tube in communication with an opening formed in the hub.

FIG. 1 illustrates one example of an inflated and expanded tamponade assembly, or tamponade balloon catheter assembly 2, inserted and positioned within a patient's anatomy. A positioning or introducer device 12 extends into the proximal end 13 of the lumen of the tamponade balloon catheter assembly 2. A drainage tube 44 is removably attached to the proximal end of the introducer device 12 leading to a collection bag 11.

Tamponade, which is the closure or blockage of a wound by applying direct pressure to the source of bleeding, is a useful method of stopping or managing bleeding or hemorrhage. One example of a known tamponade assembly includes a Bakri balloon catheter (Cook Medical, Bloomington, Ind.). The tamponade balloon catheter assembly 2, i.e., a Bakri balloon catheter, is shown as being expanded within the uterine cavity. An introducer device 12 extends within the lumen of the tamponade balloon catheter assembly 2. The introducer device 12 can remain in place within the lumen of the tamponade balloon catheter assembly 2, therefore also serving as a positioner to maintain the tamponade balloon catheter assembly 2 in place, allowing the user to reposition the tamponade balloon catheter assembly 2 during use.

Figure 2:
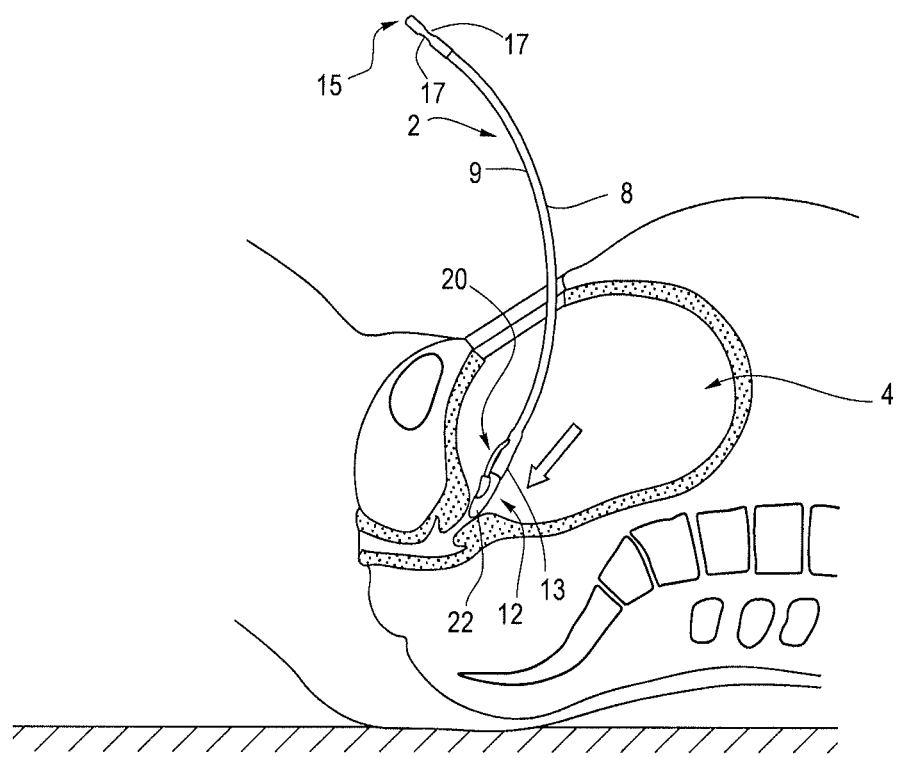
FIG. 2 is a side view of a patient's anatomy showing trans-abdominal insertion of a tamponade balloon catheter with an example of an introducer device coupled to the tamponade balloon catheter assembly.

As indicated by the arrow in FIG. 1, the introducer device 12 can be used to insert the tamponade balloon catheter assembly 2 vaginally following a vaginal birth. Alternatively, as illustrated in FIG. 2, the introducer device 12 can be employed to introduce the tamponade balloon catheter assembly 2 trans-abdominally following a cesarean birth. As shown by the arrow in FIG. 2, the introducer device 12, coupled with the tamponade balloon catheter assembly 2, can be introduced through the cesarean opening in the patient's abdominal wall and into the uterus 4. The proximal end 13 of the tamponade balloon catheter assembly 2 can then be pulled through the vaginal canal until the base of the balloon 6 (which is in a deflated state in FIG. 2) contacts the internal cervical ostium. Before inflation of the tamponade balloon catheter assembly 2, the incision may be closed, being careful not to puncture the uninflated balloon 6 while suturing.

While the tamponade balloon catheter assembly 2 is intended for placement in the uterine cavity 4 of a patient for treating and controlling postpartum hemorrhage (PPH), it may also be used in various other locations, lumens or orifices within the body, including vessels, bones, organs or other tissues, as necessary or desired. Its dimensions are alterable so that it may be appropriately dimensioned to navigate to the uterus 4, or any other target body cavity, from which fluid, such as blood, will be drained. As shown in FIG. 1, the tamponade balloon catheter assembly 2 preferably includes a catheter 8 having a longitudinal body 9 and a distal end 15 and a proximal end 13.

There is a drainage lumen 16 extending along the length of the longitudinal body 9 between the proximal 13 and distal 15 ends and, in one example, a connector (such as a Y-connector or any other suitable connector) may be located at the proximal end 13 of the catheter 8 for connecting the catheter 8 to a source of air or saline for inflation of the balloon 6 and/or for connecting the catheter 8 to a collection bag 11 or receptacle for receiving waste, fluid and/or blood drained from the patient. The catheter 8 may include one or more openings 17 at or near its distal end 15, such that when the distal end 15 of the catheter 8 is positioned in the uterus 4, the openings 17 allow blood and other fluids to enter and flow through the drainage lumen 16. The drainage lumen 16 may also be used to introduce irrigation fluid or other material into the uterus 4, such as to flush the openings 17 at the distal end 15 of the catheter 8 should they become blocked with clotted blood, tissue or other debris. The catheter 8 may also include additional ports or orifices at various points along the longitudinal body 9 to allow blood or other fluid to enter the catheter 8.

Figure 5:
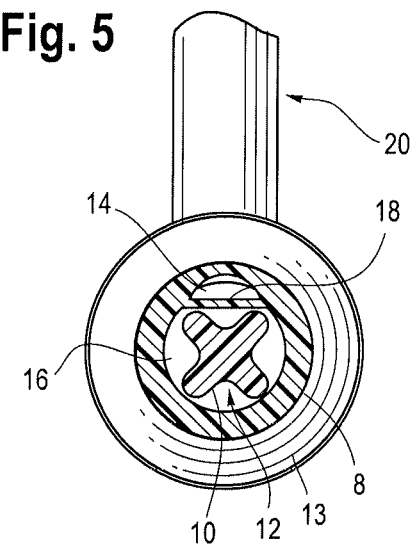
FIG. 5 is a cross-sectional view of one example of an introducer device extending through the lumen of a tamponade balloon catheter assembly taken along line 5-5 of FIG. 3.
Figure 6:
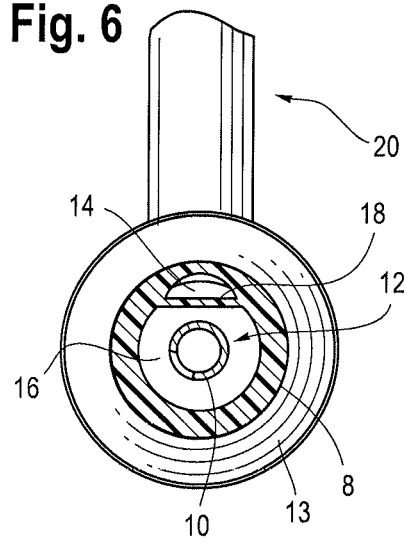
FIG. 6 is a cross-sectional view of another example of an introducer device extending through the lumen of a tamponade balloon catheter assembly.
Figure 8:
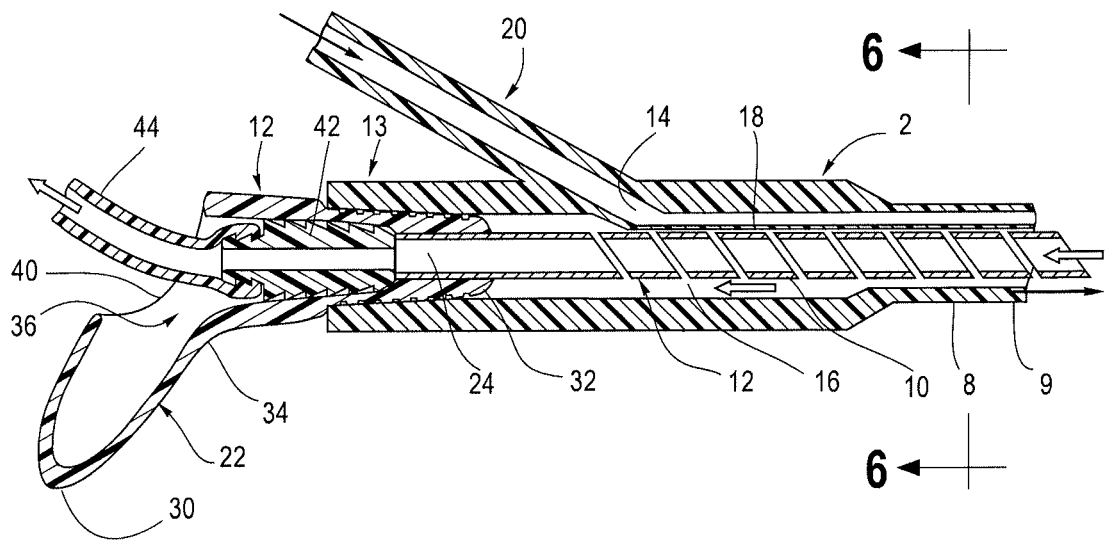
FIG. 8 is a side cross-sectional view of one example of an introducer device coupled to a tamponade balloon catheter assembly and a drainage fitting being inserted into the opening formed in the hub portion of the introducer device.

A tamponade structure, such as a balloon 6, is located near the distal end 15 of the catheter 8, and is preferably made of an expandable material such as rubber, silicone, latex or any other expansible biocompatible material. Other tamponade mechanisms may also be used in lieu of or in addition to the balloon 6, such as plurality of arms, tubes, loops, mesh or similar structures capable of expanding or otherwise conforming to the uterine cavity 4. As shown generally in FIG. 8, an inflation lumen 14 within the catheter 8 is provided to allow for inflation and deflation of the balloon 6. The inflation lumen 14 may run parallel with the drainage lumen 16, but preferably, the two lumens 14, 16 remain separate for their entire lengths and the respective lumens may generally be the same size and have similar inner diameters or, alternatively, the respective inflation lumen 14 and drainage lumen 16 may have different sizes, dimensions and/or inner diameters. In one example, as shown in FIGS. 5, 6 and 8, the drainage lumen 16 may be larger than the inflation lumen 14, such that the inner diameter of the drainage lumen 16 is shown as being greater than the inner diameter of the inflation lumen 14. Further, in one example, a septum or separating wall 18 separates the inflation lumen 14 and the drainage lumen 16. In FIGS. 5 and 6, the placement of the septum 18 results in each of the inflation lumen 14 and the drainage lumen 16 generally having a "D" shaped cross-section. However, the shape and relative size of the respective lumens 14, 16 can vary, as can the placement of the septum 18 that separates the lumens 14, 16, such that the respective lumens can have approximately the same inner diameter or different inner diameters as necessary or desired.

Figure 3:
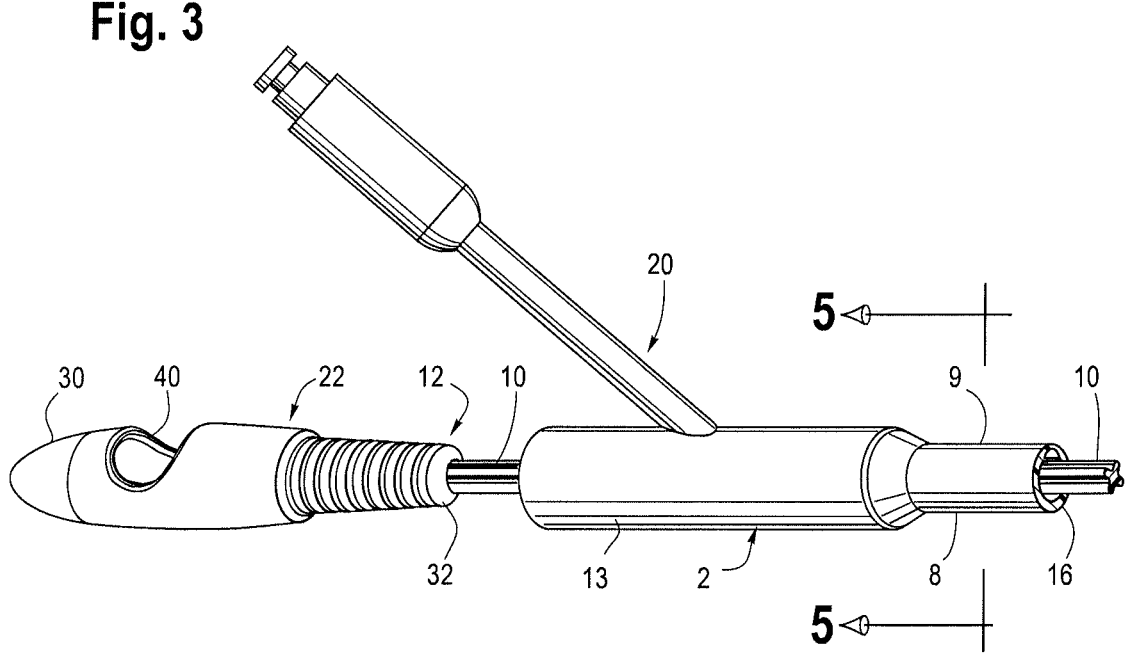
FIG. 3 is a perspective view of one example of an introducer device extending into the lumen of a tamponade balloon catheter assembly.

As shown in at least FIGS. 3 and 8, the proximal end 13 of the catheter 8 may include a branch or side arm 20. This can be one branch of the "Y" connection mentioned above. As shown in cross-section in FIG. 8, this side arm 20 is in fluid communication with the inflation lumen 14. Various media, such as water, saline, air or other physiologically compatible medium, may be introduced through the inflation lumen 14 to facilitate controlled expansion of the balloon 6. When connected to an inflation source, such as a saline bag, saline filled syringe or other inflation source, the inflation media can be introduced into the inflation lumen 14 through the side arm 20 allowing it to flow in a distal direction through the lumen of the catheter 8 and into the balloon 6, thus facilitating balloon expansion.

Once the balloon 6 has been placed within the uterus 4 of the patient, the balloon 6 may be inflated or otherwise expanded. Preferably, the balloon 6 has sufficient compliance such that, when expanded, it conforms generally to the shape and contour of the cavity in which it is placed, and when deflated, can be sufficiently reduced in profile to provide for easy passage and removal through the cervix 7 and vagina 5 (or, in the case of a cesarean birth, through the abdominal incision as shown in FIG. 2). The size and volume to which the balloon 6 may expand is preferably determined by the body cavity where hemorrhage control is needed. As shown in FIG. 1, the balloon 6 is preferably inflated with a sufficient volume and pressure such that it conforms generally to the contours of the uterine cavity 4, and more specifically, to the lower uterine segment. The inflated balloon 6 then exerts a generally uniform compressive force or pressure upon the uterine wall to substantially reduce or even stop the uterine bleeding or hemorrhage. It may also be possible to coat or impregnate all or at least a portion of the balloon surface that comes into contact with the uterine wall with biocompatible materials, drugs or other substances that may enhance or assist in controlling uterine bleeding. In one non-limiting example, this may include muscle contracting or clotting enhancing drugs or other substances that facilitate inflation/deflation of the balloon 6.

As mentioned above, the tamponade balloon catheter assembly 2 may include one or more other components or accessories. In one example, this may include an introducer device 12. The introducer device 12 may be integrally formed with and/or coupled to the tamponade balloon catheter assembly 2. Thus, an assemblage of the tamponade balloon catheter assembly 2 and the introducer device 12 can be provided to a physician directly out of the package. Alternatively, the introducer device 12 may be a separately provided component that can be inserted into catheter 8 of the tamponade balloon catheter assembly 2 and removably coupled to the proximal end 13 of the tamponade balloon catheter assembly 2 prior to or during use of the tamponade balloon catheter assembly 2.

The introducer device 12 may comprise a stylet 10 with a hub 22 located at the proximal end of the stylet 10. The stylet 10 may provide structure or added rigidity to the catheter 8 and, as previously mentioned, may be integrally formed within the catheter or, alternatively, the stylet 10 may be inserted into the catheter 8 by a physician prior to or during use of the tamponade balloon catheter assembly 2. Preferably, the stylet 10 extends longitudinally within the drainage lumen 16, or alternatively through the inflation lumen 14 or through an additional or separate lumen of the catheter 8. In one non-limiting example, the internal stylet 10 may be a hollow tube or cannula with a lumen extending there through, which provides an additional drainage conduit through which blood or other fluids draining from a body cavity, such as uterus 4, can flow.

Figure 4:
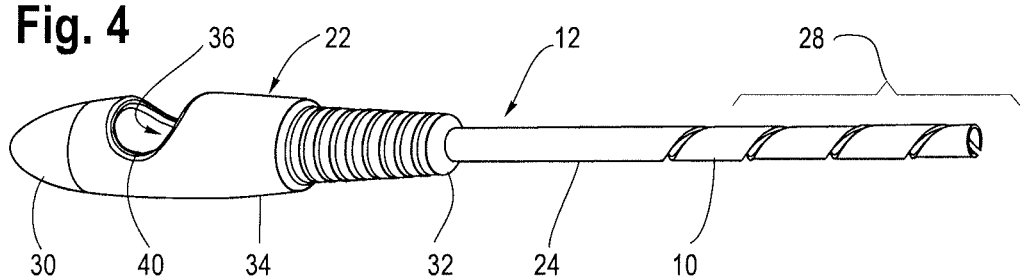
FIG. 4 is a perspective view of the proximal end of another example of an introducer device removed from the lumen of a tamponade balloon catheter assembly.

As shown in FIG. 4, in one embodiment, the stylet 10 may comprise a cannula or tube-like structure comprising metals, plastics and/or other materials that provide sufficient rigidity to maintain column strength and bolster the cannula 8. yet still flexible enough to navigate a patient's anatomy. In one example, the stylet 10 may be a stainless steel tube, coil or cannula. It is also contemplated that the stylet may be formed of other metals or metal alloys including, for example, shape memory alloys including nitinol. The stylet 10 has a proximal end 24 a distal end 26 and a middle section 28 located between the proximal and distal ends 24, 26. At least a portion of the stylet 10 may be cut or slit or otherwise incised, such as by laser cutting, electrical discharge machining (EDM), grinding or etching by known and acceptable methods. As shown in FIG. 4, a coil or helix shape has been laser cut and/or ground in at least the middle section 28 of the stylet 10, but it is also contemplated that the stylet 10 can be cut, ground or etched the entire length between the proximal and distal ends 24, 26 or any portion thereof in between. The grinding, etching or cutting may be continuous, but it can also be segmented such that uncut stylet segments are located between one or more slit, cut or etched segments. In other words, uncut segments of the stylet may be interspersed between cut segments.

In one example, it is contemplated that the helix shape incised in the stylet 10 has an aspect ratio in the range of approximately 2:1 to 4:1 between the inner diameter and wavelength, and preferably about 3:1, where the inner diameter of the tube is approximately 4 mm and the wavelength of one helix is approximately 12 mm. However, other shapes and configurations and ratios of the etching or cutting are contemplated as necessary to provide the desired combination of attributes and characteristics, including, but not limited to, column strength, stiffness, torsion, flexibility and malleability of the stylet 10 for the intended use. The helical-shaped cut in the stylet 10 permits fluid draining from the uterus to flow freely through the lumen of the drainage catheter 8 as well as through and around the cuts in the stylet 10. In other words, fluid flowing through the drainage lumen 16 can also flow within the lumen of the stylet 10, through the helical cuts, slits or etches and along the exterior surface of the stylet 10 when the stylet 10 remains in place within the drainage lumen 16 of the catheter 8.

This can also be accomplished with a stylet 10 that may be formed in a spring-like or coil configuration, which can also provide sufficient column strength and flexibility as well as allow adequate drainage of fluids flowing proximally from the uterus 4 through the drainage lumen 16 and through and around the stylet 10 positioned within at least a portion of the drainage lumen 16. In one example, a stylet 10 having a spring-like coil configuration may have an aspect ratio of approximately 1:12 where the inner diameter of the tube is approximately 4 mm, and the wavelength of one helix is approximately 0.33 mm. In other embodiments, the stylet may have a series of parallel slits oriented horizontally, vertically, diagonally or combinations thereof, or the stylet 10 may include a sinusoidal shaped cut, or combinations thereof, for example.

FIG. 3 illustrates another embodiment of the stylet 10. As shown there, the stylet 10 may be formed of a polymeric material, such as plastic, by molding, casting and/or extrusion. In other examples, the stylet 10 may be formed of aramid fiber reinforced composites, carbon fiber reinforced composites, graphene composites, metal matrix composites and combinations thereof. The stylet 10 may have a cruciform or "+" shaped cross-section which allows fluid to pass through the annular space between the spokes of the stylet 10 within the drainage lumen 16 of catheter 8 in which the stylet 10 resides. In other words, in a cruciform cross-section, the stylet 10 includes at least two and preferably three, four or more arms or spokes extending radially outwardly from a center hub point or longitudinal axis. In another example, the stylet 10 may have a cross-sectional shape that is a modification of the cruciform cross section in which more than four arms or spokes extend radially outwardly from the longitudinal axis. In this way the cross section of the stylet 10 may resemble spokes or arms that result in an asterisk-like cross-section (e.g. "*") or similar shape having a hub and spoke type of configuration. In addition to the above-disclosed embodiments, the stylet 10 may be a variety of other shapes and configurations, solid or hollow, and made of suitable biocompatible materials including plastics, metals and/or composites and combinations thereof.

In this way, the various embodiments of the stylet 10 shown in both FIGS. 3 and 4, for example, can be left in place within the drainage lumen 16 of catheter 8 during use of the tamponade balloon catheter assembly 2 to treat hemorrhage. In other words, the introducer device 12 does not have to be removed from the lumen of the tamponade balloon catheter assembly 2 in order to allow fluid to drain from the uterine cavity 4. However, if necessary or desired, the introducer device 12 can be removed from the tamponade balloon catheter assembly 2 during use and then re-inserted into the lumen of the catheter 8 to aid in the repositioning and/or removal of the tamponade balloon catheter assembly 2 when hemorrhage ceases and use of the tamponade balloon catheter assembly 2 is complete.

The stylet 10 may run the entire length or at least a portion of the length of the catheter 8, and extend to a location adjacent to or just distal of the openings 17 at the distal end 15 of the catheter 8, for example, or at least extend a sufficient length so as to add longitudinal stability to the catheter 8. Sufficient column strength of the stylet 10 provides pushability while reducing or substantially eliminating unwanted folding and/or bending of the catheter 8, while also resisting and preventing longitudinal shortening, shrinkage and/or collapse during trans-vaginal insertion (and/or insertion through a C-section incision) and during positioning of the balloon 6 within the uterus 4. The stylet 10 also has sufficient flexibility and malleability so as to navigate the contours of a patient's anatomy without causing damage, tearing or trauma.

As shown generally in at least FIGS. 3 and 4, the introducer device 12 may further comprise a hub portion 22 at the proximal end 24 of the stylet 10. The hub 22 comprises a proximal end 30 and a distal end 32 and a sidewall 34 extending there between that defines a lumen 36. The distal end 32 of the hub 22 may be integrally formed with the proximal end 24 of the stylet 10 or it may be separately formed and attached to or over-molded on to the stylet 10 such as by bonding, adhesives and/or other suitable attachment mechanisms. The hub 22 may be coaxial with the axis of the stylet 10 or the hub 22 may be offset or angled from the proximal end 24 of the stylet 10. In one example, the hub 22 may be formed of a biocompatible elastomer, including but not limited to a polymeric molding or casting having a durometer soft enough to be pliable and provide for sealing with other components or fittings (such as a drainage tube 44 and/or drainage fitting 42) yet stiff enough to have pushability during insertion of the introducer device 12 into the patient during use. In one example, the hub 22 may have a durometer of approximately 39 shore A to approximately 85 shore A and preferably approximately 52 shore A. The hub 22 may be formed of a polymer such as urethane or silicone or it may be formed of a co-polymer. Other materials may also be used to form the hub 22 including rubbers and plastics.

Figure 7:
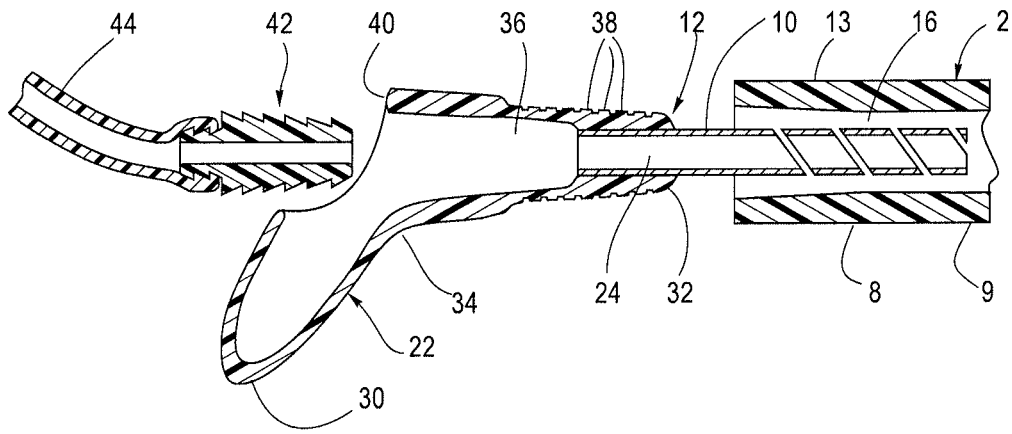
FIG. 7 is a side cross-sectional view of one example of an introducer device being inserted into the lumen of a tamponade balloon catheter and a drainage fitting being inserted into an opening formed in the hub portion of the introducer device.

As illustrated in FIG. 7, the distal end 32 of the hub 22 may be tapered. One or more ribs, threads or ridges 38 may be present on at least a portion of the exterior surface of the hub 22, at least at the distal end 32 thereof. The tapered distal end 32 of the hub 22 is preferably shaped for removable attachment or coupling to the proximal end 13 of the catheter 8. For example, the ribbed exterior surface at the distal end 32 of the hub 22 may be inserted into (or otherwise engaged with, such as by barbs, threads and/or other corresponding engageable surfaces) the proximal end 13 of the catheter 8 as shown in FIG. 8. In this way, the tamponade balloon catheter assembly 2 and the introducer device 12 can be coupled and move together as a unit to provide convenient and efficient insertion, positioning and repositioning of the tamponade balloon catheter assembly 2 in the uterus 4. The distal end 32 of the hub 22 may remain in place within the proximal end 13 of the catheter 8 such as by interference fit or friction fit or corresponding threads, barbs or sealing surfaces located within the proximal end 13 of catheter 8, although other methods of attachment between the respective components may also be used.

Figure 9:
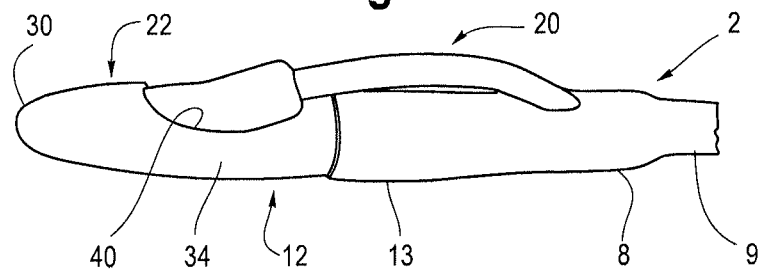
FIG. 9 is a perspective view of a hub portion of an introducer device that is coupled to a tamponade balloon catheter assembly with the inflation port at the proximal end of the tamponade balloon catheter assembly received within an opening formed in the hub.

The hub 22 may have at least one opening or aperture 40 formed therein. The hub opening 40 may be formed in any portion of the hub 22 between the proximal and distal hub ends 30, 32, however, as shown in FIGS. 7 and 8, the hub opening 40 is formed in a side wall 34 of the hub 22 at a location that is generally centered between the proximal and distal hub ends 30, 32. The hub opening 40 provides an aperture into which a drainage fitting 42 can be removably attached, as shown in FIGS. 7 and 8. In one example, the drainage fitting 42 is a barb fitting but it is contemplated that any fitting for removable attachment with the hub opening 40 may be used. Alternatively or in addition to providing an aperture or opening 40 for placement of a drainage fitting 42 during use of the tamponade balloon catheter assembly 2, the hub opening 40 may also provide an aperture for receiving the inflation port or side arm 20 extending from the proximal end 13 of the catheter 8. The side arm 20 can be removably secured within the hub opening 40 of the introducer device 12 as shown in FIG. 9, such as by friction fit or interference fit, during insertion of the tamponade balloon catheter assembly 2 into the uterus 4 as shown in FIGS. 2 and 9. The hub 22 may include other openings or apertures in addition to opening 40 to allow for additional points of drainage or inflation and/or to allow additional tubes or catheters to be removably attached to the hub 22 and placed into fluid communication with the catheter 8 when the introducer device 2 is coupled to the tamponade balloon catheter assembly 2 as shown in FIG. 8.

When the balloon 6 is deployed within the uterine cavity, the outward force of the balloon 6 against the uterine wall helps to resist dislodgement of the balloon 6 from the uterus 4. However, the rigidity provided to the catheter 8 of the tamponade balloon catheter assembly 2 by the internal stylet 10 prevents longitudinal collapse of the catheter 8, such that at least the portion of the catheter 8 located between the balloon 6 and the hub 22 of the introducer device 12 will maintain structural integrity and longitudinal length. This prevents longitudinal shrinkage or collapse of the longitudinal catheter body 9 when force is exerted on it in either a proximal and/or distal direction, such as in the event that the uterus 4 attempts to "deliver" the balloon 6 through an insufficient cervix (thus exerting pressure on the catheter body 9 in a proximal direction) and/or when a physician pushes the catheter 8 into the uterus 4 during insertion (thus exerting pressure on the catheter body 9 in a distal direction). In essence, the stylet 10 provides a scaffold to bolster the catheter 8 during introduction, positioning and use of the tamponade balloon catheter assembly 2.

Turning now to FIGS. 1 and 2, introduction of a tamponade balloon catheter assembly 2 such as the Bakri balloon catheter, with an introducer device 12, may be as follows. Before the uterine tamponade balloon catheter assembly 2 is inserted into a patient, the introducer device 12 may be inserted into the proximal end 13 of the tamponade balloon catheter assembly 2 and the hub 22 coupled to the proximal end 13 of the tamponade balloon catheter assembly 2. Alternatively, the introducer device 12 may be pre-loaded into the tamponade balloon catheter assembly 2 so that the tamponade balloon catheter assembly 2 coupled to the introducer device 12 is ready to use as a unit right out of the package. As shown in FIGS. 2 and 9, the inflation port or side arm 20 at the proximal end 13 of the tamponade balloon catheter assembly 2 can be removably secured within the hub opening 40 of the introducer device 12 during insertion of the tamponade balloon catheter assembly 2 into the uterus 4, such as by friction fit or interference fit. In other words, with the hub 22 of the introducer device 12 located just proximal to the proximal end 13 of the tamponade balloon catheter assembly 2, the side arm 20 of the tamponade balloon catheter assembly 2 that provides a port for inflation of the balloon 6 during use can be tucked into the hub opening 40 to maintain the tamponade balloon catheter assembly 2 in a low profile and compact delivery configuration to prevent the side arm 20 from interfering with the introduction of the tamponade balloon catheter assembly 2 or from snagging on tissue, especially during a "hub-first" trans-abdominal insertion into the uterus as shown in FIG. 2.

Following a vaginal birth, the tamponade balloon catheter assembly 2, with the introducer device 12 in place within a lumen of the tamponade balloon catheter assembly 2, may be inserted "balloon first" through the vagina and into the uterus 4 as shown in FIG. 1. Alternatively, following a cesarean birth, the tamponade balloon catheter assembly 2, coupled to an introducer device 12 in place within a lumen of the tamponade balloon catheter assembly 2, may be inserted "hub first" through the abdominal incision as shown in FIG. 2. The hub 22 and the proximal end 13 of the tamponade balloon catheter assembly 2 can be pulled through the vaginal canal until the base of the balloon 6 contacts the internal cervical ostium.

With the balloon 6 in its desired position in the uterus 4, the side arm 20 can be removed from its position where it has been tucked and held within the hub opening 40. The balloon 6 may then be inflated or otherwise expanded with a physiologically suitable fluid through the inflation lumen 14 of catheter 8. The shape of the fully expanded balloon 6 will generally conform to the shape of the interior of the uterus 4, and preferably the lower uterine segment, thus exerting a compressive force against the uterine walls. In one example, the balloon 6 may be quickly and carefully inflated with 200 to 500 milliliters of saline. The balloon 6 may be partially or fully deflated to allow repositioning, if necessary. Packing may also be added to the vagina, or traction may be applied to the shaft of the catheter 8 to increase effectiveness of the tamponade balloon catheter assembly 2.

The introducer device 12 may remain in place within the drainage lumen 16 of the tamponade balloon catheter assembly 2 during use, if desired. Blood or other fluids draining in a proximal direction through the catheter 8 from the uterus 4 may flow through the lumen 36 formed in the hub 22 and exit the hub 22 through hub opening 40. As shown in FIGS. 7 and 8, a drainage tube 44 is removably attached to the hub opening 40 by a drainage adapter fitting 42 that has been inserted into the hub opening 40 and is snugly and securely held in place in the hub opening 40 such as by friction fit, interference fit or other suitable attachment means or mechanisms. As shown generally in FIGS. 7 and 8, the hub 22 is sufficiently pliable and flexible to allow the user to bend back or otherwise manipulate at least the proximal end 30 to open or widen the hub opening 40 to allow for the ease of insertion and removal of a drainage adaptor fitting 42 (as well as insertion and removal of the side arm 20 as described above) and any other tubes, adaptors, fittings or accessory devices that the user may wish to place into fluid communication with the hub opening 40. However, other suitable mechanisms for securing the drainage adaptor fitting 42 in place may be used. Blood and other fluids draining proximally through the hub 22 can continue flowing through the drainage adaptor fitting 42 and into the drainage tube 44 for collection in waste collection bag 11. The volume and flow of fluid into the waste collection bag 11 can be monitored to determine when hemorrhage is reduced or has ceased. Upon adequate cessation of hemorrhage as determined by the physician, the balloon 6 may be quickly drained through the drainage lumen 16 to deflate the balloon. The tamponade balloon catheter assembly 2 can then be removed from the patient trans-vaginally.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A positioning device comprising:
   a stylet comprising a longitudinal body having a proximal end and a distal end;
   a hub at the proximal end of the stylet, the hub comprising a proximal end, a distal end and a sidewall extending there between, the sidewall comprising an uninterrupted curvilinear configuration defining an outer surface of the hub, a hub lumen extending between the proximal and distal ends, wherein the curvilinear sidewall of the hub comprises at least one opening formed therein, an inflation port extending from a proximal end of a catheter and wherein a proximal end of the inflation port is removably received within the at least one hub opening when the distal end of the hub is coupled to the proximal end of the catheter.

2. The device of claim 1 wherein the stylet comprises a lumen extending at least partially between the proximal and distal ends and wherein the hub lumen is in communication with the lumen of the stylet.

3. The device of claim 1 wherein the stylet comprises a tubular cannula and wherein at least a portion of the longitudinal body comprises at least one of a cut, a slit, an opening, a ground surface and an etched surface formed therein.

4. The device of claim 3 wherein the stylet comprises a helical shaped cut in the longitudinal body extending at least partially between the proximal and distal ends of the stylet.

5. The device of claim 1 wherein the stylet is a stainless steel coil.

6. The device of claim 1 wherein the stylet is comprised of at least one of a metal, a metal alloy, a polymer and a co-polymer.

7. The device of claim 1 wherein the stylet comprises a cruciform cross-sectional shape.

8. The device of claim 1 wherein the distal end of the hub comprises a tapered outer surface.

9. The device of claim 8 wherein the tapered outer surface of the hub comprises at least one of threads, ribs, coupling mechanisms, barbs, flanges, channels and projections.

10. The device of claim 1 wherein the proximal end of the hub comprises an atraumatic tip.

11. The device of claim 1 wherein the hub comprises a biocompatible polymeric material.

12. The device of claim 1 wherein the stylet is configured to extend longitudinally within a lumen of a catheter tube.

13. The device of claim 1 wherein the hub opening is configured to removably receive at least one of a valve, adapter, fitting and tubing segment.

14. A catheter assembly comprising:
a positioning device comprising:
a stylet having a proximal end and a distal end; and
a hub at the proximal end of the stylet, the hub comprising a proximal end, a distal end and a sidewall extending there between, the sidewall comprising an uninterrupted curvilinear configuration defining an outer surface of the hub, a hub lumen extending between the proximal and distal ends, and wherein the curvilinear sidewall of the hub comprises at least one opening formed therein,
a tamponade balloon catheter comprising:
a catheter comprising a proximal end and a distal end and at least one lumen extending there between;
an expandable tamponade device at the distal end of the catheter;
an inflation port extending from the proximal end of the catheter;
wherein the stylet is configured to extend longitudinally within at least a portion of the at least one catheter lumen; and
wherein a proximal end of the inflation port is removably received within the at least one hub opening when the distal end of the hub is coupled to the proximal end of the tamponade balloon catheter.

15. The assembly of claim 14 wherein the at least one lumen comprises a drainage lumen and wherein the catheter further comprises an inflation lumen.

16. The assembly of claim 15 wherein the drainage lumen and inflation lumen run parallel to each other and are separated by a septum.

17. The assembly of claim 14 wherein the distal end of the hub comprises a tapered outer surface that is configured to be coupled to the proximal end of the catheter.

18. The assembly of claim 14 wherein the hub lumen is in fluid communication with the at least one catheter lumen.

* * * * *